United States Patent
Arzanpour et al.

(10) Patent No.: US 8,734,153 B2
(45) Date of Patent: May 27, 2014

(54) INTELLIGENT DENTAL HANDPIECE CONTROL SYSTEM

(75) Inventors: Siamak Arzanpour, Surrey (CA); Vahid Zakeri, Surrey (CA)

(73) Assignee: Simon Fraser University, Burnaby (*) Notice: Subject to any disclaimer, the term of this patent is extended or adjusted under 35 U.S.C. 154(b) by 119 days.

(21) Appl. No.: 13/088,219

(22) Filed: Apr. 15, 2011

(65) Prior Publication Data

US 2011/0256496 A1 Oct. 20, 2011

Related U.S. Application Data

(60) Provisional application No. 61/324,709, filed on Apr. 15, 2010.

(51) Int. Cl.
*A61C 3/00* (2006.01)

(52) U.S. Cl.
USPC .............. 433/114; 433/99; 433/103; 433/131

(58) Field of Classification Search
USPC .............................. 433/27, 114, 99, 103, 131
See application file for complete search history.

(56) References Cited

U.S. PATENT DOCUMENTS

| | | | |
|---|---|---|---|
| 4,723,911 A | 2/1988 | Kurtz | |
| 5,538,423 A | 7/1996 | Coss et al. | |
| 5,980,248 A | 11/1999 | Kusakabe et al. | |
| 6,491,522 B1 | 12/2002 | Jensen | |
| 6,665,948 B1 | 12/2003 | Kozin et al. | |
| 6,929,476 B2 | 8/2005 | Katsuda et al. | |
| 7,022,123 B2 | 4/2006 | Heldreth | |
| 7,249,952 B2 | 7/2007 | Ranta et al. | |
| 7,369,916 B2 | 5/2008 | Etter et al. | |
| 8,004,664 B2 | 8/2011 | Etter et al. | |
| 2006/0106482 A1 | 5/2006 | Etter et al. | |
| 2006/0118315 A1* | 6/2006 | Suzuki et al. | 173/2 |
| 2007/0190484 A1 | 8/2007 | Brennan et al. | |
| 2008/0145817 A1 | 6/2008 | Brennan et al. | |
| 2008/0193893 A1* | 8/2008 | Beck | 433/27 |
| 2008/0254404 A1* | 10/2008 | Heraud | 433/27 |
| 2009/0155735 A1 | 6/2009 | Hauger | |
| 2009/0253094 A1 | 10/2009 | Thompson et al. | |
| 2010/0143861 A1 | 6/2010 | Gharib et al. | |
| 2011/0020084 A1 | 1/2011 | Brett et al. | |

* cited by examiner

*Primary Examiner* — Eduardo Colon Santana
*Assistant Examiner* — Bickey Dhakal
(74) *Attorney, Agent, or Firm* — IProperty Inc.

(57) ABSTRACT

An intelligent dental handpiece control system is disclosed. The handpiece includes a sensor which detects a vibration, sound, force or torque frequency/time signal produced by the handpiece in use and signal processor which produces or determines secondary signal characteristics such as the handpiece torque, force or angular velocity. A controller analyzes the secondary signal characteristics and produces a control signal which controls or stops the angular velocity of the dental handpiece in order to avoid overdrilling of healthy tooth material or damaging the nerves in the jaw during dental implant operations. The controller may also provide a warning signal to the user and/or control the angular velocity of the handpiece.

20 Claims, 12 Drawing Sheets

Dental handpiece cutting control strategy schematic

FIG. 1.  Comparison of the frequency response of Accelerometer, Laser Doppler Vibrometer (LDV) and Microphone FIG. 2. Effect of vertical downward cutting on rotational bearings of powered dental handpiece FIG. 3. Frequency analysis of dental handpiece for cutting material with no horizontal advancement FIG. 4. Effect of horizontal cutting on rotational bearings of powered dental handpiece FIG. 5. Frequency analysis of dental handpiece while cutting material with horizontal advancement FIG. 6. Frequency analysis of dental handpiece while cutting material under high applied force and with horizontal advancement FIG. 7. Frequency analysis of dental handpiece while cutting material under low applied force and with horizontal advancement FIG. 9. Dental handpiece cutting control strategy schematic FIG. 10.    Multiple material sample schematic design

INTELLIGENT DENTAL HANDPIECE CONTROL SYSTEM

1. CROSS-REFERENCE TO RELATED APPLICATIONS

The present application claims priority to previously filed U.S. Provisional Patent Application No. 61/324,709 filed Apr. 15, 2010 and entitled INTELLIGENT DENTAL HANDPIECE CONTROL SYSTEM, the contents of which are hereby incorporated by reference in their entirety.

2. TECHNICAL FIELD

The present invention relates generally to a dental handpiece control systems. More particularly, the present invention relates to a control system for a dental handpiece designed to avoid over drilling of materials such as dental caries and dental restorative material.

3. BACKGROUND OF THE INVENTION

Tooth decay, also known as dental caries, is one of the most common human diseases, after the common cold, and affects all age groups. Dental caries is caused by acid erosion of tooth enamel, typically resulting in a carious lesion or cavity in the tooth enamel, or underlying dentin or pulp. A dental filling, also called a dental restoration, is an emplacement of non-native material in a tooth, and is a process used to retain the functionality, integrity and morphology of tooth structure. The dental restoration process typically involves removing the carious and/or infected tooth material, usually using a handheld dental handpiece (a high speed handheld drill), filling the resulting cavity in the tooth with one or more dental restoration materials, and forming the restoration material to the desired shape in the tooth before it solidifies to form the completed restoration. Dentists are trained to be experts at interpretation of their tactile and visual senses as one of their only tools to manage and manipulate the tools (such as the dental handpiece or drill) used to perform the tooth restorations as well as other daily dental operations, many of which may require the precise removal of undesired carious or otherwise diseased tooth material, while leaving adjacent healthy or desired tooth material undamaged and intact. The high rotational speed of modern powered dental handpiece tools, small available space in the patient's mouth for maneuvering such tools particularly to reach remotely located caries in the mouth, and the necessity of working on conscious patients are key factors that affect the accuracy and reliability of a dentist's use of their tactile and visual senses to control the removal of tooth material during a procedure. If the additional factors of dentist's periodic fatigue and humans' typically slow responses to sudden changes, are also considered in light of the fact that powered dental handpieces can easily remove a large portion of a tooth with a small motion of the wrist or fingers (or due to movement by the patient), then the problem of accurately controlling the process of removing tooth material with a powered dental handpiece typically becomes even more serious. It can therefore be concluded that with current restoration and treatment routines, the undesired loss of dental structure due to inadvertent over-removal of healthy tooth material may be common and inevitable. It should be emphasized that tooth structure is one of the few parts that the body that is not biologically reproduced or healing, and that therefore any undesired loss of tooth structure will be permanent. Similar to removing dental caries, the replacement of restorations may result in the loss of healthy dental structure.

X-ray and clinical tactile and visual bases identification techniques are the principal tools used by dentists to detect cavities or other diseased tooth areas; however, such diagnostic tools typically do not reveal complete information regarding the depth and/or size of caries or other lesions, particularly at depth within a tooth. Therefore, such current diagnostic and control methodologies may typically be insufficient to provide a dentist with the ability to optimally and selectively remove tooth material throughout common dental restoration procedures. Further, dental restorations are not just limited to cavity removal and filling processes. Although dental fillings may not degrade particularly quickly, external forces imposed on restorations such as by clenching or grinding of teeth causes fatigue of the restoration structure, leading to development of cracks and ultimately failure. The performance of dental restorations may typically be subject to several factors, including the performance and characteristics of restorative materials used, the dental practitioner's level of experience, the type and position of tooth, the restoration's shape, size and number of restored surfaces, and the patient's age and health. If an old filling or other restoration collapses, there is a high potential for developing new decay that requires removal and replacement of the old restoration and removing any related further decay or cavities. Replacing of old restorations is still one of the most frequently performed procedures in clinical dental practice and which typically exceeds in number the removal and restoration of new carious lesions. The high rate of required removal and replacement of old restorations does not appear to have declined in spite of all modern advancements in the field of dental restoration materials. Replacing a dental restoration, however, does not exclude the likelihood of the same imperfections occurrence, nor the prevention of new lesions and/or secondary caries from eventually occurring in the newly replaced restoration. Similar to the original removal of dental caries, the replacement of previous restorations may frequently also result in undesired loss of healthy dental structure due to poor identification and selective removal of restoration and/or diseased tooth material particularly through use of powered dental handpiece tools.

The most commonly used dental restorative materials are amalgam and composites. Dental amalgam is low cost, easy to handle and inhibits the growth and reproduction of bacteria. The rate of amalgam fillings has recently declined due to adverse health concerns. This has created a shift in restorative dentistry toward use of composite materials. Although high quality composite restoration materials and better restoration techniques have improved their longevity, restoration replacement rates have continued to become significantly higher and the evolution of caries in composite restorations is typically faster than in amalgam based restorations. This appears to indicate that more restoration replacements and even more resultant undesired tooth structure loss due to the perfect color matching of composite restorations to the surrounding original tooth, which may further complicate the ability of dentists to accurately identify and selectively remove restoration material separate from desired tooth structure material.

In addition to procedures related to caries removal and dental restorations, a further dental procedure for which additional assistance is desirable for dental practitioners is in relation to installation of dental implants. In a dental implant procedure a dental practitioner typically makes a small hole inside the patient's jaw and in several steps then enlarges the opening sufficiently to prepare it for insertion of a dental implant. During the dental implant installation procedure dental practitioners typically cannot see inside the hole in the patient's jaw, and instead typically rely solely on their tactile senses. Such "blind" operation presents a real danger that if the dental handpiece enlarges the implant cavity too much or extends it too deeply, nerve damage may occur with potentially permanent and serious consequences for the patient.

Accordingly, there remains a need for techniques and apparatus to improve the ability to selectively identify and remove desired dental materials such as decayed or diseased tooth (caries and/or cavities) material, restoration material and healthy original tooth material from one another, and to improve control of powered dental handpiece tools in performing such removal.

4. BRIEF SUMMARY OF THE INVENTION

According to one embodiment of the present invention, an intelligent dental handpiece control system is provided that can detect and discriminate between tooth structure, dental caries, dental restoration materials, and hard/soft tissue structure and then controllably selectively remove at least one chosen material from within a patient's mouth preferably without damage or removal of unintended surrounding material. In one such embodiment, the intelligent dental handpiece control system may desirably detect and discriminate between dental caries and dental restoration material and tooth structure, and may then provide for selective removal of dental caries and/or dental restoration material substantially without removing and/or damaging surrounding tooth structure materials. One of the advantages of such selective dental handpiece control system design according to one embodiment of the invention, as is further explained below, is that it desirably requires no new components be added to existing commercially available powered dental handpieces (or drills) in order to provide the desired selective removal control capabilities. In one embodiment of the present invention, microphones (exemplary of a non-contact sensor means) may be used for sensing and collection of data characteristic of the function of the dental handpiece. In one embodiment, a command signal may be generated by a suitable controller that analyzes and processes the handpiece data and suitably adjusts and/or controls the power to the dental handpiece to control the cutting and/or removal of dental materials by the dental handpiece in a patient's mouth.

In another embodiment of the invention, the intelligent dental handpiece control system may desirably provide for material recognition by means of at least one contact and/or non-contact sensor for sensing dental handpiece characteristic data, analysis of such dental handpiece characteristic data and integration of this sensing and material recognition with a suitably rapid actuated control system to control the force, movement and/or power of the dental handpiece during removal of the intended dental material within a patient's mouth. In one embodiment, the intelligent dental handpiece control system may desirably analyze differences between the force applied manually by a practitioner for advancement of a dental handpiece during cutting of dental material, and the handpiece torque required for cutting such material, and may desirably apply such analysis to accurately distinguish and identify different dental materials (caries, restoration or tooth structure), and to implement a command scheme to provide selective cutting or removal of the intended dental material(s). In a particular embodiment, a relationship between the force applied to the dental handpiece in order to advance the handpiece during material cutting/removal, and the handpiece torque required during cutting a particular material may be used in the identification of individual tooth materials online during use, and for controlling the dental handpiece through rapidly responsive power management of the dental handpiece.

In one embodiment of the present invention, the intelligent dental handpiece control system may be applied to commercially available air-turbine type dental handpieces in use with commercially available and typical material cutting bur tools, for example. However, in further embodiments, the dental material sensing, recognition, and handpiece control system of the invention may also be applied to other types of powered dental handpieces, such as commercially available electric dental handpiece designs, for example. In yet a further embodiment of the present invention, the intelligent dental handpiece control system may comprise identification of a relation between dental material type and angular velocity of the dental handpiece during removal of material, estimation of handpiece cutting force by analysis of the frequency response spectrum and/or time response signal of the dental handpiece, condition monitoring of the dental handpiece during use, online recognition of dental material being removed, and control of the dental handpiece (such as control of one or more of force, movement and/or power of dental handpiece) to implement selective material cut or removal, for example.

5. BRIEF DESCRIPTION OF THE DRAWINGS

The embodiments of the intelligent dental handpiece control system according to the present invention will now be described with reference to the accompanying drawing figures, in which.

Like reference numerals refer to corresponding parts throughout the several views of the drawings.

6. DETAILED DESCRIPTION OF THE INVENTION

Figure 1:
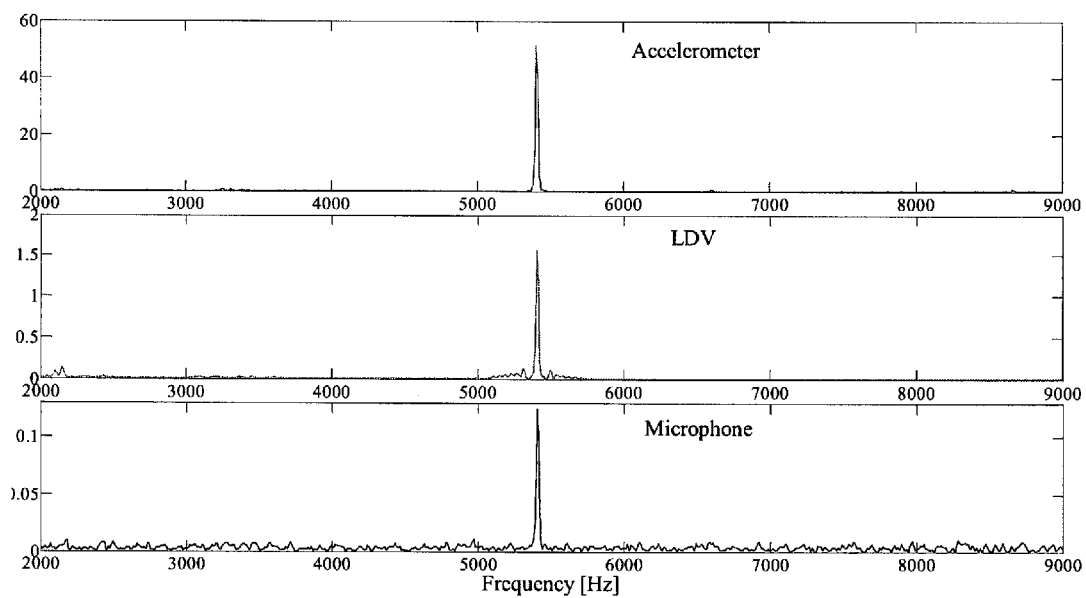
FIG. 1 illustrates a comparison of the frequency responses of three suitable sensors in response to a free-running dental handpiece according to the invention.

As detailed above, there remains a need for an dental handpiece control system which allows for control of the removal of dental materials in order to reduce inadvertent and undesired removal of tooth structure while allowing removal of dental caries and/or existing dental restoration materials, and accordingly to improve dental restoration practice and improve patient oral health. Such a system may also be used in dental implant procedures such as to avoid damage to the nerves in the jaw. Accordingly, in one embodiment of the present invention, an intelligent dental handpiece control system is provided that enables discrimination between dental materials online during use of a powered dental handpiece and is controlled to selectively cut or remove a desired type of dental material while reducing and/or minimizing removal or damage of undesired dental materials such as tooth structure, for example. In one such embodiment, the inventive dental handpiece control system desirably provides online information regarding the identification and removal of the dental material affected by the dental handpiece during the cutting process.

In dentistry, factors controlling the removal of dental material may typically include at least two interrelated factors:

1) torque applied to the cutting tool (such as a commercially available dental handpiece bur tool), and 2) pushing force (typically from a dental practitioner's hand) applied to the handpiece to advance the cutting action of the handpiece through the dental material being cut.

When a pushing force is applied to a dental handpiece in order to advance a cutting tool such as a bur through a dental or jaw material being cut, there may typically be a reduction in angular velocity, or rotational speed, of the dental handpiece related to the force applied to the handpiece, due to the torque applied to the cutting tool by the dental material being cut. In the present patent application, for simplicity, the source of the angular velocity reduction due to the cutting of a dental material is hereinafter referred to as the "cutting torque". Further, in the present application, the force applied to the dental handpiece to advance the cutting action of the handpiece is hereinafter referred to as the "cutting force".

In one embodiment of the present invention, the intelligent dental handpiece control system analyzes the magnitude of the cutting torque and of the cutting force, during cuting of a dental material, taking into consideration operating parameters of the dental handpiece such as rotational speed (rpm) and cutting tool type (such as a bur type), in order to provide an identification of the type of dental material being cut by the cutting tool during a dental material cutting procedure. In one embodiment, in order to detect and/or measure the cutting torque and cutting force, known miniaturized torque and force sensors may be retrofitted to a dental handpiece. However, in some other applications, due to the small and high speed nature of many modern powered dental handpieces, such retrofitting of sensors in contact with the handpiece may be undesirable, such as due to the increased size, weight, complexity and failure risk of such a retrofitted handpiece incorporating such contact sensors, and further potentially be undesirable due to a reduction of maneuverability and tactile feedback provided by such a retrofitted dental handpiece during use. In such other applications then, the use of non-contact sensors may be preferred.

In a further embodiment of the present invention, the use of one or more non-contact sensors for detection and measurement of cutting force and cutting torque may be provided as a practical solution which avoids the need to retrofit a commercially available dental handpiece for use in accordance with an embodiment of the inventive intelligent dental handpiece control system. In such an embodiment, a non-contact sensor may be applied to detect accessible data characterizing the function of a dental handpiece in use, such as the characteristic vibrations and sounds produced by a dental handpiece during use. Use of such a microphone sensor may desirably provide a characteristic signal source from which a frequency/time analysis of the dental handpiece sound signals may provide a rich source of information about the condition of a dental bur tool, the air turbine (or electric motor in the case of an electric dental handpiece), handpiece tool drive shaft, and handpiece rotational bearings, for example. In one embodiment, such exemplary contact and non-contact sensors that may typically be employed for measuring such charactistic handpiece vibration and sound signals (typically high frequency) may include accelerometers, Laser Doppler Vibrometers (LDVs) and microphones, for example.

In such an embodiment, the frequency responses of three potential contact and non-contact sensors (accelerometer, LDV, and microphone) in response to a free-running dental handpiece are shown for comparison in FIG. 1, with the X axis indicating frequency in Hz, and the Y axis being mm/s$^2$ for acceleration; mm/s for LDV applications; and dB for the microphone results, respectively. The resulting frequency responses show the significant consistency in all measurements regardless of the particular type of non-contact sensor employed, and therefore, a general embodiment, accelerometers, LDVs, microphones, or other equivalent contact and non-contact vibration and/or sound sensors may be used interchangeably in embodiments of the inventive system such as are further described below. In one embodiment of the present invention, microphones may be used as an exemplary non-contact sensor since they do not require contact or immediate proximity to the dental handpiece, and are not limited by the requirement of line-of sight for focussing light paths, as may be required by some other types of sensors.

Figure 2:
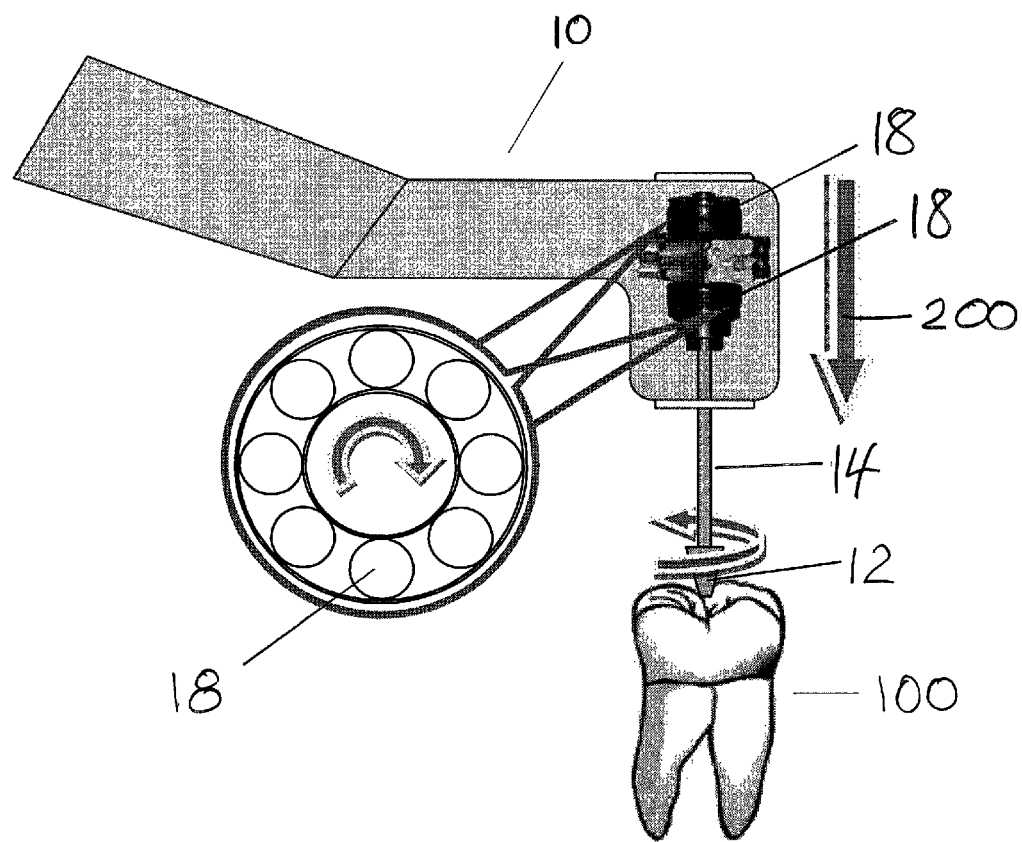
FIG. 2 illustrates measurements of the frequency spectrum of a dental handpiece in use to cut a dental material using a non-contact sensor according to an embodiment of the invention.
Figure 3:
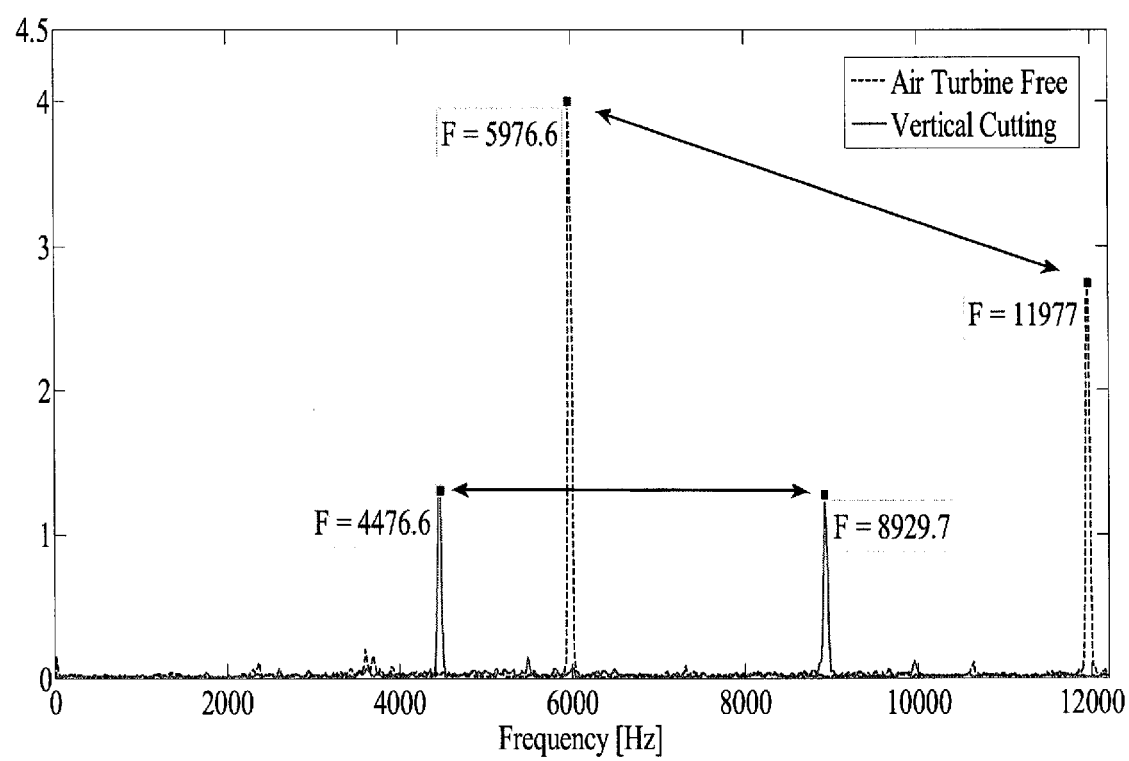
FIG. 3 illustrates a frequency spectrum of a dental handpiece measured by a non-contact microphone sensor according to an embodiment of the invention.

In a first embodiment, measurements of the frequency spectrum of a dental handpiece 10 in use to cut a dental material using a non-contact microphone sensor (not shown) are shown in FIG. 2 according to a first orientation where a dental handpiece cutting bur 12 is used to cut a dental material 100 in a vertical direction, where no horizontal force is applied to the bur 12 to advance the cut in a horizontal direction, but instead the dental handpiece 10 and cutting bur 12 are moved only vertically in alignment with the axis of rotation of the tool shaft 14 and bur 12. Accordingly, there are no lateral forces applied to the rotational bearings of the dental handpiece 10 as shown in FIG. 2. The bearings 18 of the dental handpiece 10 are also shown, and the effect of downward cutting 200 on the rotational bearings 18 of the dental handpiece 10. A frequency spectrum of the dental handpiece 10 in FIG. 2 measured by a non-contact microphone sensor is shown in FIG. 3. It may be observed that the first peak in the frequency spectrum as shown in FIG. 3 corresponds to the actual angular velocity of the dental handpiece and that the other higher frequency peaks in the spectrum are harmonics of the first peak. It is also important to note that the amplitude of the frequency peaks are significantly above the background noise level ($\leq 60$ dB) which simplifies the accurate location and identification of the frequency peaks in the response data.

In one embodiment, the frequency spectrum analysis of the handpiece sound (FIG. 3) which contains information about the angular velocity of the handpiece, may be used to identify the type of dental material being cut in the cutting process (such as shown in FIG. 2). It is known from experimentation that the angular velocity of a commonly available air turbine dental handpiece drops the moment its cutting bur makes contact with and begins to cut a dental material, however, the dilemma is that the detectable angular velocity reduction is a function of both the dental material properties and also the rate of advancement of the handpiece and the cutting force applied to cause the advancement, which exerts friction and a resultant torque against the rotational bearings of the dental handpiece. In fact, it has been found that a low cutting advancement rate on a hard material may result in a substantially similar detectable reduction in handpiece rotational velocity as a higher cutting advancement rate on a softer material. As a result determining the reduction in angular velocity of the dental handpiece is not enough by itself to unambiguously allow identification of the dental material being cut.

Accordingly, in association with one embodiment of the present invention, a methodology is provided that identifies the relationship and contribution of cutting force (force applied to result in a particular rate of cutting advancement) and cutting torque (related to the type of dental material) to result in a particular measured or detected reduction in angular velocity of the dental handpiece. In one such embodiment, the fundamental differences between the effects of cutting force and cutting torque on the handpiece rotational bearings may be determined in order to provide for effective identification of a dental material being cut. In one embodiment, such cutting torque and cutting force values may be measured directly using suitable sensors. However, in many applications, such direct measurement of torque and/or force may not easily be implemented in a dental handpiece, and in such cases indirect force and torque measurement techniques may be employed. For example, in a first embodiment where dental material is cut with no horizontal advancement, such as shown in FIG. 2, the detected reduction in angular velocity of the handpiece is primarily due to cutting torque exerted on the handpiece tool 10 resulting from dental material removal. This can be simulated by moving the handpiece 10 substantially parallel to the axis of revolution of the bur 12, as shown in the vertical cutting orientation of FIG. 2. In such case, the rotational load may typically be distributed substantially evenly on all of the balls of the rotational bearing 18 and the boundary conditions of the rotational bearing 18 may be expected to remain almost the same as in a control case where the handpiece bur is run free without contacting dental material. As shown in FIG. 3 according to such an embodiment, the detected or measured frequency spectrum of the dental handpiece sound confirms that such vertical cutting orientation results in substantially similar rotational bearing loading because in both frequency spectra illustrated in FIG. 3, the fundamental frequency and its first harmonic peak for the vertical cutting case are simply shifted to left as a result of the detected reduction of the angular velocity due to material cutting. The Y axis of FIG. 3 shows dB. The frequency peaks are indicated by an "F" notation with a specific dB reading.

Figure 4:
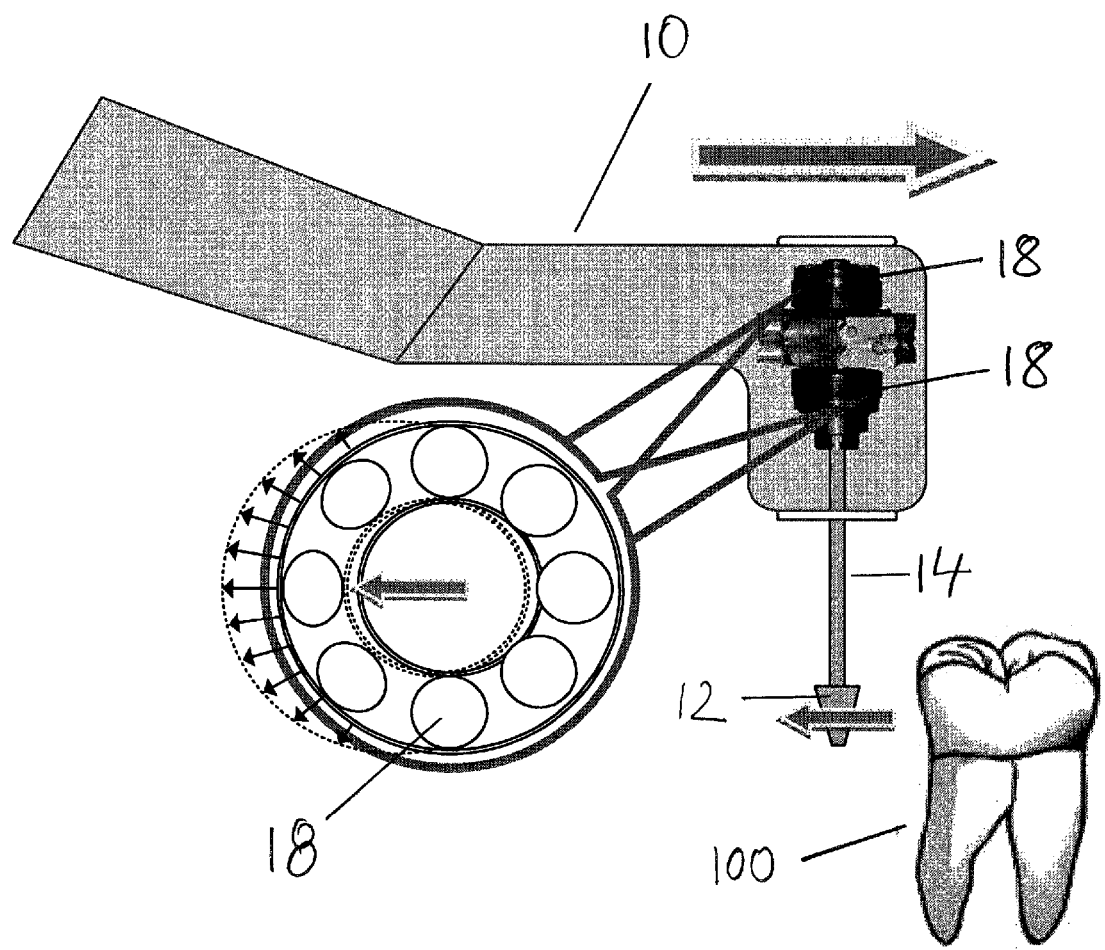
FIG. 4 illustrates a side view of a dental handpiece and bur with a horizontal force applied by the hand of a practitioner according to an embodiment of the invention.

In a further embodiment of the invention, a case where an external force applied by a practitioner's hand, for example, results in a horizontal cutting advancement of the handpiece 10 as illustrated in FIG. 4. In such an embodiment, however, the boundary conditions of the rotational bearings 18 of the handpiece 10 are changed from the vertical cutting or free running conditions, due to the creation of a lateral directional loading concentration zone to one side of the rotational bearing 18 that compresses the bearing balls passing through it and relaxes the others on the opposite side (see FIG. 4). In such an embodiment, the new rotational bearing boundary condition is dependent on the horizontal cutting force applied, and accordingly, it is expected that the consequent new peaks created in the detected frequency spectrum of the handpiece sound describe characteristics of the applied horizontal cutting force. In a particular exemplary embodiment, a dental handpiece was moved perpendicular to the axis of rotation of the cutting bur to cut dental materials in a horizontal advancing direction by the application of a horizontal cutting force.

Figure 5:
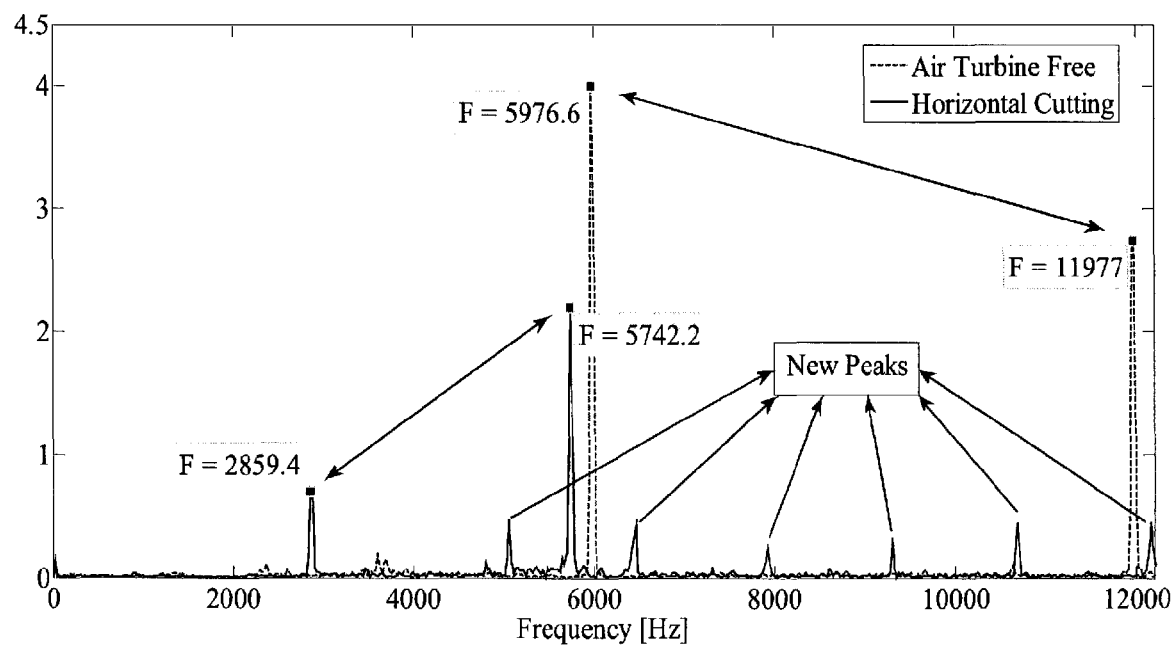
FIG. 5 illustrates the first and second harmonics and new peaks of the angular velocity of the handpiece during horizontal cutting according to an embodiment of the invention.
Figure 6:
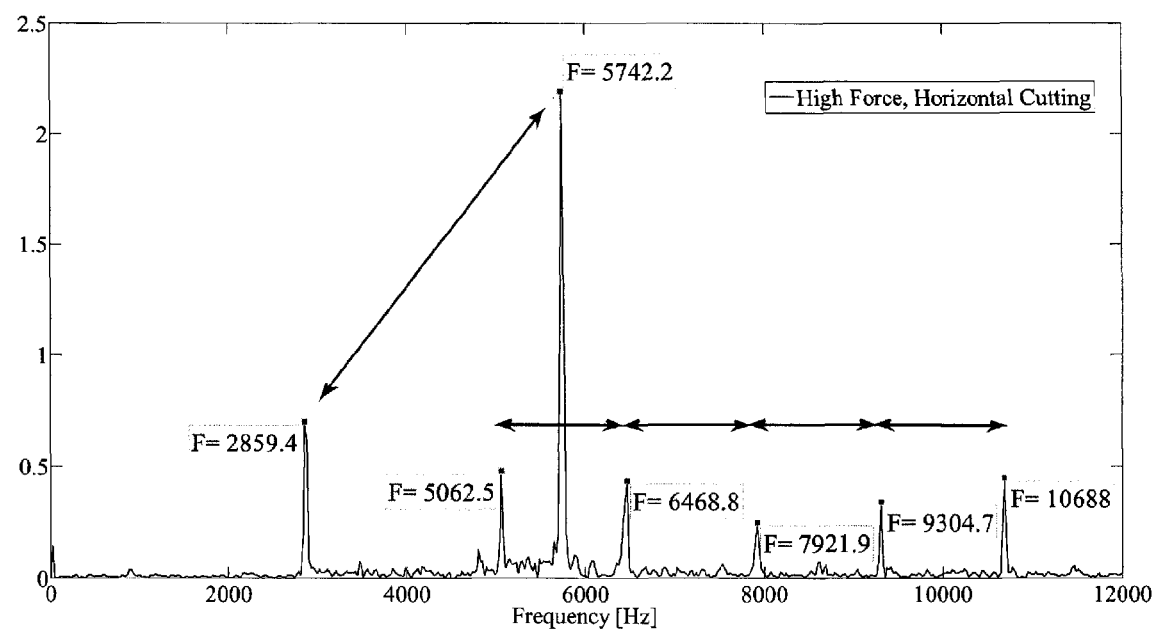
FIG. 6 illustrates a frequency analysis of the dental handpiece while cutting material under a high applied force and with horizontal advancement according to an embodiment of the invention.
Figure 7:
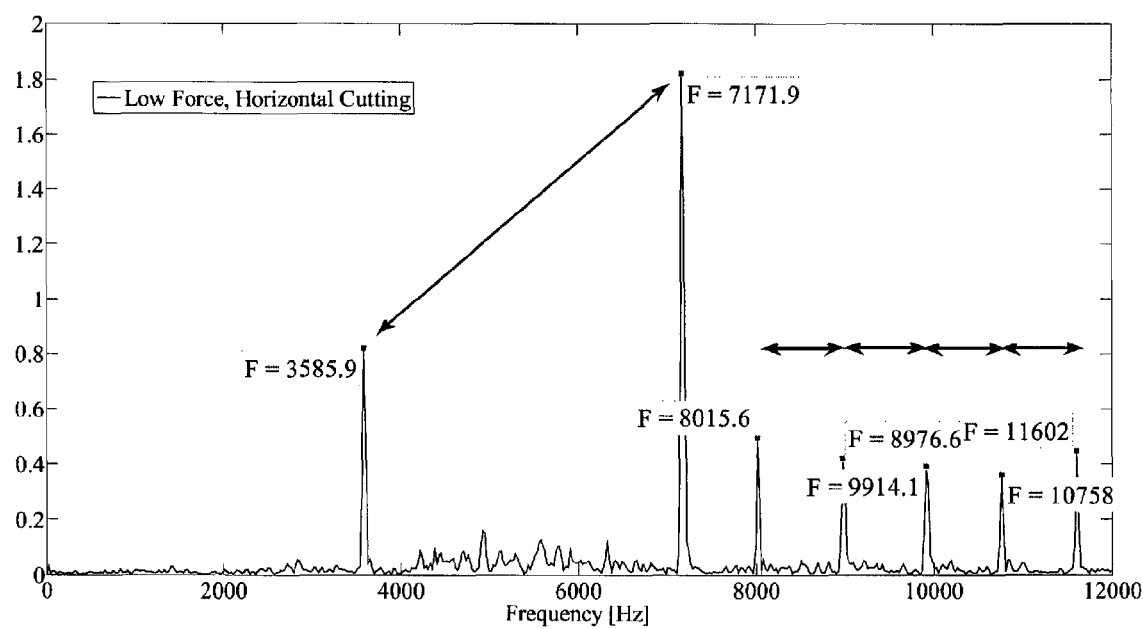
FIG. 7 illustrates a frequency analysis of the dental handpiece while cutting material under a low applied force and with horizontal advancement according to an embodiment of the invention.

The experimentally derived frequency spectrum results are depicted in FIG. 5 (dB on Y axis) which indicate the first and second harmonics of the angular velocity of the handpiece during horizontal cutting (reduced from the free-running angular velocity) as well as new frequency peaks with approximately equal spacing distances in the spectrum. In such an embodiment, the dependency of the detected frequency peaks to the horizontal cutting force applied to the handpiece may be determined by repetition of the horizontal cutting experiment at a different cutting force or load magnitudes, resulting in the detected frequency spectrum results of which are shown and compared in FIG. 6 and FIG. 7. The effect of the variation in horizontal cutting force applied to the dental handpiece can be seen in these experiments by considering the distance between the frequency peaks as shown in FIG. 6 and FIG. 7, where it can be seen that as the cutting force applied increases, the distance between the frequency peaks in the detected frequency spectrum also increases accordingly. In one embodiment, this distance between detected frequency peaks in the dental handpiece frequency spectrum during cutting of dental material may be calibrated to obtain the magnitude of the cutting force applied to the handpiece to advance the cutting tool through the dental material.

Accordingly, in one embodiment of the present invention, the contribution to the detected reduction in handpiece angular velocity due to the applied cutting force may be determined as noted above, and this contribution may be deducted from the detected current reduction in handpiece angular velocity during cutting (corresponding to the location of the first harmonic frequency peak) to determine the angular velocity reduction portion that is due to the cutting torque applied against the handpiece by the type of dental material being cut, thereby providing for the determination of the type of dental material being cut by its characteristic cutting torque. Therefore, in one embodiment, the frequency spectrum analysis of the response of a non-contact microphone sensor to the sound of a dental handpiece in use for cutting dental materials may be used (when calibrated as described above) to determine both the cutting force applied to the handpiece, and also the cutting torque applied against the handpiece by the dental material and which may be used as a characteristic property to identify the type of dental material being cut. The amplitudes of the additional frequency peaks resulting from the applied cutting force and its effect on the rotational bearings of the handpiece are also significantly higher than the background noise (≤20 dB), which makes their identification more certain and useful for detection and analysis ultimately determining the material type.

In other optional embodiments, the above-described application of a non-contact sensor (such as a microphone, for example) to detect and through analysis to determine applied force and characteristic torque values for a rotating shaft tool, may be used in other applications where it may be difficult to use or install contact sensors or may be desirable to use non-contact type sensors, for example. Exemplary such applications of bearing supported rotating shaft tools may be found in fields such as oil, water or other drilling, cutting/milling machinery, turbines and turbomachinery, and automotive applications.

The sensor and signal processor may be integral to the dental handpiece, or may be externally located. Additionally, a dental handpiece control kit including a vibration (and/or sound/force/torque) sensor operable to detect a vibration (and/or sound/force/torque) frequency/time signal produced by the handpiece in use; a signal processor operable to process the vibration frequency/time signal and produce secondary signal characteristic(s); a controller operable to analyze the secondary signal characteristic(s) and produce a control signal; and a power controller operable to control the angular velocity of the dental handpiece may also be provided, in order that existing handpieces may be retrofitted or used in conjuction with the control system.

According to a further embodiment of the present invention, aspects of the intelligent dental handpiece control system include (1) Dental handpiece characterization, i.e. material-cutting torque relation to enable identification of cutting material, (2) Dental handpiece vibration (and/or sound, force or torque) signature characterization, i.e. cutting force calibration to enable isolation of cutting torque values for material identification purposes, and (3) Control algorithm development to allow automated or assisted control of dental handpieces in use.

Dental Handpiece Characterization

In accordance with one embodiment of the present invention, the angular velocity reduction of a dental handpiece during cutting of a dental material (such as dental caries, dental restoration materials, enamel, dentine, pulp, or bone, for example) due to the cutting torque applied to the handpiece by the material being cut may be characterized for a variety of dental materials, and such characteristic angular velocity reductions may desirably be related to the individual types of dental materials and their properties in order to enable their identification based on characteristic such angular velocity reductions.

Dental Handpiece Power-Torque-Angular Velocity Relations

According to one embodiment, in order to recognize specific dental materials from the angular velocity reduction of the handpiece due to the effect of cutting torque is determining the relationship of power-torque and angular velocity in a range of typical and common commercially available dental handpieces, such as in particular air turbine handpieces. Such relationship is determined using a miniature size dynamometer for example, wherein the power to the dental handpiece can be varied over a testing range by changing the air supply pressure such as by using a regulator. Thereby, the cutting torque may be determined using the known power and angular velocity of the handpiece, using the power relationship in air turbines.

Known Material-Cutting Torque Characterization

Similar to as described above, in one embodiment of the invention, if a dental handpiece starts cutting dental material without advancement, the angular velocity of the handpiece drops and may be detected by a contact and/or non-contact sensor such as an accelerometer or microphone, for example. The new angular velocity corresponds to a new torque in the graph indicating the remainder of the cutting power of the handpiece as well as that used for cutting. This reduction due to cutting torque exerted in pure cutting without advancement through the material can be calibrated as a characteristic property for different types of relevant dental materials to provide for their recognition based on angular velocity reduction values. Although the information about the cutting torque is not directly useful for material identification, by entering the data into the controlling algorithm of the present invention, which compares the real-time data to a database of experimentally derived characteristics of different dental materials, the torque and power of the dental handpiece can then be adjusted automatically or selectively by the operator, such as based on an alarm, for selective cutting of the material.

Figure 8:
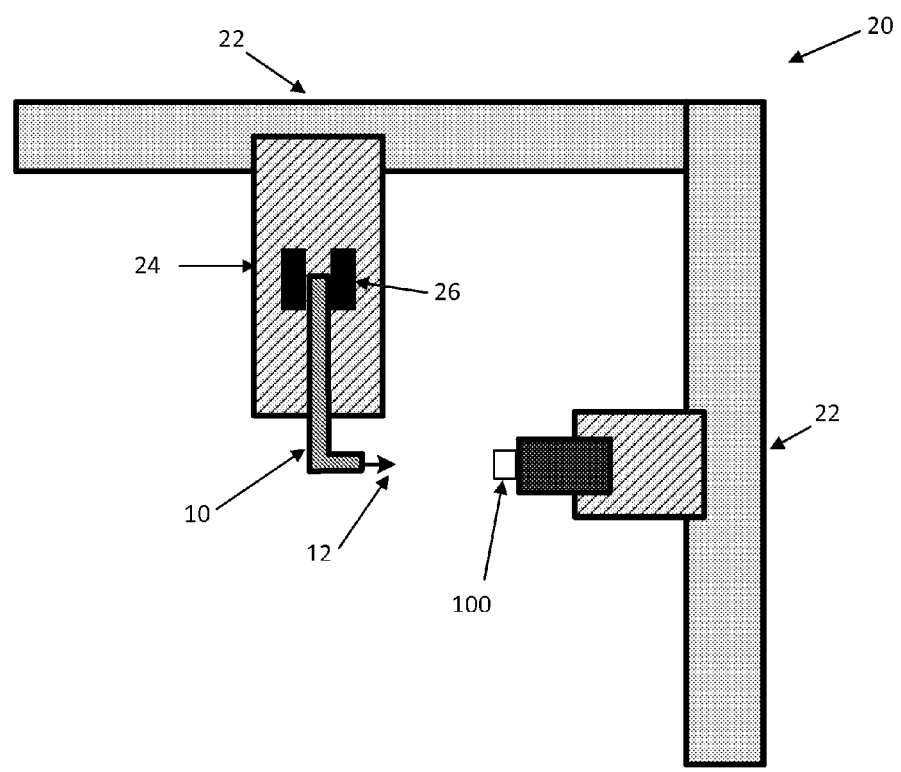
FIG. 8 illustrates a side view of a dental handpiece X-Y control stage apparatus according to an embodiment of the invention.

To avoid complexity and to provide substantially consistent samples of dental material properties, samples from isotropic dental materials with known characteristics may be used for characterization according to one embodiment of the invention. Samples may be placed in a two dimensional X-Y dental handpiece stage to allow for controlled cutting of the dental material sample with the dental handpiece, and for measuring the angular velocity frequency response and power/torque of the dental handpiece while cutting the material in a controlled setting. An example of such a two dimensional X-Y control dental handpiece stage 20 suitable to provide controlled cutting and material characterization testing is shown in FIG. 8. The linear actuators 22, rotary table 24, force plate 26 and test dental material 100 are also shown. The dental handpiece 10 may then be used to cut the dental material samples in a direction substantially aligned with the axis of rotation of the handpiece tool (similar to as shown in FIG. 2) at a very slow and controlled pace and the angular velocity of the handpiece bur 12 may be recorded. Following sufficient such characterization testing, a suitable mathematical or other model may be selected that best relates the material properties of the dental material 100 like hardness and elasticity to the measured correlated handpiece angular velocity reduction (cutting torque). Such findings may then be optimally modified for application to anisotropic materials with known properties i.e. wood. In such case, the intensity of anisotropy is optimally considered by testing different materials and also by varying cutting angle of the handpiece tool. Accordingly, a set of characteristic material property-angular velocity reduction relations is compiled for relevant dental materials that can also capture the effect of anisotropy as well as its intensity.

Tooth Material-Cutting Torque Characterization

In one exemplary embodiment of the present invention, a further step may comprise tooth or dental material 100 identification based on the angular velocity reduction of a dental handpiece 10 while cutting the tooth 100. In one example of such a step, samples from real extracted and preserved teeth may be used for characterization of variations in dental handpiece angular velocity. For such characterization the crown portions of the preserved tooth may be used as a sample for tooth enamel material. A KaVo® Key Laser 3+ or other suitable cutting device may be used to precisely cut the crown of the tooth to produce characterization samples. Samples from tooth dentine material may also be obtained after the crown is cut. Such characterization samples may be placed in an epoxy which subsequent to solidification acts as a fixture to retain the sample during characterization testing. The sample may then be tested on a suitable handpiece characterization test stand 20, such as an exemplary two dimensional X-Y stage as illustrated in FIG. 8. Characterization experiments may be conducted for different dental bur 12 designs and orientations to determine variations and calibrations required due to the effect of individual bur tool 12 characteristics. In another exemplary embodiment, characterization sample preparation for common dental restorations materials may easily and advantageously be made such as by forming into any desired testing shapes, however in one embodiment to save costs, small cavities into epoxy may be made for sample preparation.

Preparing exemplary characterization samples for dental caries materials and their identification by typically require more preparation before characterization experiments and testing proceeds. In one embodiment, caries samples may be artificially developed on extracted tooth materials such as by using decalcification techniques. Various such decalcification and/or demineralization protocols are available to remove calcified matrix and soften the hard tissue, such as decalcification with EDTA Ethylenediaminetetraacetic acid), a chelating agent, which advantageously provides a relatively less invasive method of hard tissue decalcification. In one such protocol, a 20% concentration of EDTA in buffer may be used over the course of at least about a week with vigorous agitation at room temperature to decalcify an average size tooth. Teeth may be embedded in plastic (epon/epoxy) or wax at the roots, leaving a portion of the crown exposed in preparation, then immersed in the decalcifying solutions in order to decalcify only specific areas of the occlusal surface of the tooth. Such decalcification processes may desirably be monitored with radiographs so that similar images of tooth decay becomes visible, such as to provide a substantially consistent caries material sample and associated properties. Following such preparation, samples may be tested according to substantially the same procedure described above for enamel and dentine tooth materials for characterization according to one exemplary embodiment.

Effects of Dental Bur and Water

In accordance with one embodiment of the invention, the relation of the detected frequency spectrum of the sounds of a dental handpiece bur tool to the dental bur's relative roughness and size as well as to use in wet or dry conditions during cutting of tooth materials in employed to diagnose boundary layers between materials. This relationship provides distinct boundaries in the tooth material/angular velocity regions of test results. In an alternative embodiment, the inventive intelligent dental handpiece control system may desirably include a bur library or database comprising all commonly used bur tools and their relative characteristics and calibrated effects on detected frequency spectra of dental handpieces. In such case, a dentist may simply select the bur they are currently using from the list in order to take into account the effects and characteristics of the chosen bur on the frequency analysis during use. In a further optional embodiment, bur tools may be automatically detected and compensation for their characteristics automatically made (burs may be color coded for easy identification) from the detected difference between the free run angular velocity of each type of bur such as due to their distinct moment of inertia when rotated in a dental handpiece. According to one embodiment of the invention, following such above-described characterization testing, a set of angular velocity/material database for desired and/or relevant dental materials may be established for use in the intelligent dental handpiece including such relevant dental materials such as caries, composite and amalgam restorations, and tooth structure such as including enamel, dentine and/or pulp.

Dental Handpiece Vibration Signature Characterization

In accordance with an embodiment of the present invention, the cutting force applied by to a dental handpiece to advance the cutting of the handpiece through tooth materials is determined and corrected for the identification of tooth material types by the inventive control system by first characterizing and calibrating the frequency/time response (such as by analysis of the response signal peaks and/or peak pattern) to the handpiece characteristics and also by identifying the contribution of the cutting force in the total angular velocity reduction of the handpiece during cutting such as may be detected by frequency/time response analysis of the vibration/sound signal produced by the handpiece in operation.

As described previously above, the cutting force applied to the handpiece induces a new pattern in the frequency response spectrum of the handpiece sound as detected by a sensor such as a microphone. The frequency/time response (such as comprising distinct signal peaks) due to the cutting force are typically suitably recognizable above the background noise levels. The distance between such additional frequency peaks may then be related to the intensity of the applied cutting force.

Peak Location Identification

In one embodiment, if the frequency analysis method of material identification is selected, searching for the peaks in the frequency domain (such as shown in FIG. 6 and FIG. 7) response of the handpiece sounds may be achieved by defining a suitable threshold level (preset or adaptive) as is known in the art, since the peaks that are related to the cutting force may typically be considerably higher than the background noise. Analysis of the dental handpiece sound exhibits a unique frequency response spectrum for a dental handpiece in use. Optionally, the sensitivity of the frequency response to potential sources of noise may be determined, and in a case where results indicate high noise sensitivity the frequency response may be preprocessed to reduce the effect of such noise, such as by: 1) noise filtration or 2) adaptive pattern-based signal processing. In yet a further embodiment, analysis may be based on the fact that detected frequency peaks, resulting from either the angular velocity or the applied cutting force, follow patterns, such as showing harmonics. Accordingly, in such embodiment a search algorithm may be applied to disqualify irrelevant peaks and to clarify the frequency analysis.

Following identification of the frequency peaks, the frequencies of the peaks may then be classified as related to either the angular velocity of the handpiece, to the cutting force applied to the handpiece. In one embodiment, such classification of the cause of such frequency peaks may be completed based on the fact that the cutting force related peaks typically appear at higher frequencies than the first harmonic of the angular velocity. As a result, the first harmonic of angular velocity and its higher harmonics in the spectrum are determined. This may advantageously reduce the list of frequency peaks to those correspond to the applied cutting force. The interval between such frequencies can be found and calibrated such as described previously above to determine the magnitude of the applied cutting force.

Cutting Force Frequency Interval Calibration

According to one exemplary embodiment of the invention, a calibration process for applied cutting force determination may be performed on a suitable testing platform, such as an exemplary two dimensional X-Y dental handpiece stage 100 as shown in FIG. 8. The linear actuators 22 of such stage may be programmed to move the platform at fixed velocities, for example, and all applied cutting forces and cutting torques may accordingly be measured such as by a 6-axis load cell (Nano 17, SI-50-0.5) which desirably has a very fine resolution. In one such embodiment, the distance between the applied cutting force related peaks may typically be determined by calibrations based on the 6-axis load cell measurements. To lower the level of measurement uncertainty, in one embodiment isotropic materials with known properties may be used first. Several further experiments may be conducted corresponding to small handpiece advancement rates and the calibration factor(s) for the applied cutting force may thereby be obtained. In another embodiment, identification of the magnitude of the applied cutting force may be made by subtracting the handpiece angular frequency reduction due to the tooth material type (such as described above) from the total detected reduction in angular velocity, and by attributing the remaining portion of the angular velocity reduction to the cutting force. This determined contribution of the applied cutting force on the detected angular velocity reduction of the handpiece may then be used by a controller such as a dental handpiece control module, to identify the unknown tooth material being removed in the cutting process.

Effect of Dental Handpiece Defects

Dental handpieces are typically high speed cutting tools. The ball bearings of modern handpieces are typically very small and may be particularly sensitive to the external cutting forces applied on their inner ring, such as illustrated in FIGS. 6-8. Also, dental handpieces may typically be exposed to autoclave sterilization after each dental procedure, which may accelerate the wear and/or fatigue rate of the bearings. Accordingly, small defects in the rotational bearings of a handpiece may typically appear as a small out of axis rotation (wobble) of the bur tool. Such minor axial deviation or wobble may be dangerous since it increases the cutting envelope and width of kerf cut by the bur and may consequently contribute to operational mistakes such as overcutting, for example. Such defects may also affect the precession of the applied cutting force calibration since both defects and applied cutting forces act to change the boundary condition of the rotational bearings and produce new peaks in the frequency response spectrum. According to a further embodiment of the invention, the signal history of a handpiece tested over multiple sterilizations to accelerate wear may be processed to show the trend of defect evolutions in dental handpieces, may also help to identify a practicable threshold to capture it automatically. Such processing and analysis related to handpiece defects may desirably also be a part of the intelligent dental handpiece control system according to an embodiment of the invention, however it may also be independently useful in the field of understanding defects and their evolution in dental handpieces. Accordingly, in one embodiment of the present invention, the above-described procedures may be implemented in an intelligent dental handpiece control system that is operable to receive the signals of the microphone as the inputs, analyze and process the signal, and estimate the applied cutting force and identify the material type being cut.

Controller Design and Implementation:

According to an embodiment of the present invention, a dental handpiece controller is provided that 1) discriminates the type of dental material being cut during use of the handpiece and 2) Adjusts the input power to the handpiece to cut selectively and/or prevent cutting of undesired dental materials.

Control Algorithm Development

Figure 9:
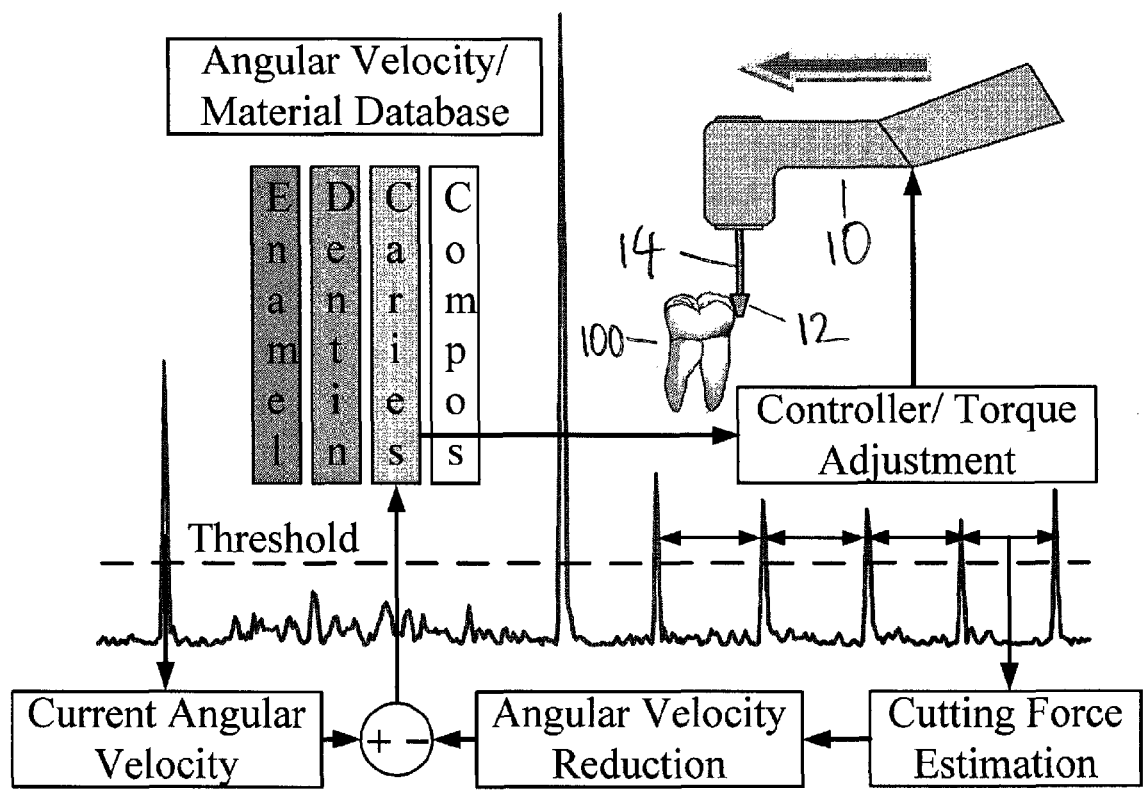
FIG. 9 is a schematic view of a dental handpiece cutting control strategy according to an embodiment of the invention.

In one such embodiment, the control unit may be composed of a fast response pneumatic valve that is commanded by a controller module. In such a case the inputs to the controller module may comprise dental material type identification and applied cutting force that are identified from signal processing of the handpiece sound as described above, and as shown in FIG. 9. The controller module then determines based on the identified material type whether to cut the material or to stop the handpiece bur tool, such as by cutting power to the dental handpiece (in the case of an air turbine handpiece, such as by cutting air flow to the handpiece). For allowing cutting, the controller may open the controlled valve(s) to provide enough cutting torque to the handpiece in order to cut the dental material as required. For preventing cutting of the material, the controller may desirably adjust and/or set the valve, so that any torque provided to the handpiece is not sufficient to cut that particular dental material. In such a case, the valve may not be completely shut down since such complete shutdown may result in undesirable delay for the handpiece and bur to re-accelerate to a working velocity following detachment from the material to be saved and reintroduction to a material to be cut.

In one embodiment, proportional pneumatic valves may be controlled by the controller in order to provide control of pneumatic power delivered to the handpiece, however in such a case a concern may include the potential response time of such a valve in order to restrict the power to the handpiece should the material be determined not to be cut (cost may comprise a concern for proportional valves in some embodiments). In a further embodiment, Pulse Width Modulation (PWM) may also be used to control the velocity of the dental handpiece turbine and therefore the cutting bur tool. In one such embodiment, the desirably low cost and fast response PWM method may be implemented using a solenoid valve that actuates at about 80 Hz to create air flow pulses and to controllably drive the handpiece turbine and bur. The airflow provided to power the handpiece may be adjusted by controlling the pulse duration of the airflow pulses. In other embodiments, further modifications are also possible by arranging a bypass low-cost pneumatic proportional valve in parallel with the PWM solenoid system. In such applications the controller may switch between the two valves depending on the fluctuation (fast response) or steady state (slow response) situations required to control the cutting power of the handpiece. In an alternative embodiment of the invention applied to an electric dental handpiece, the handpiece power control can be achieved by adjusting the electrical power supplied to the device.

Control Methodology Verification

Figure 10:
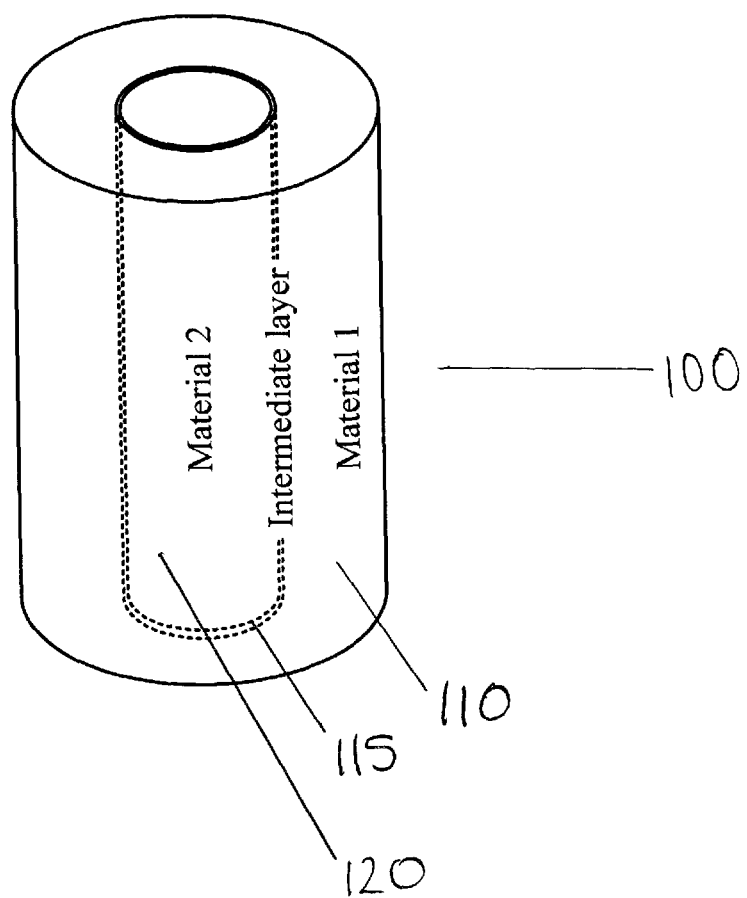
FIG. 10 illustrates a perspective view of a multiple material sample.
Figure 11:
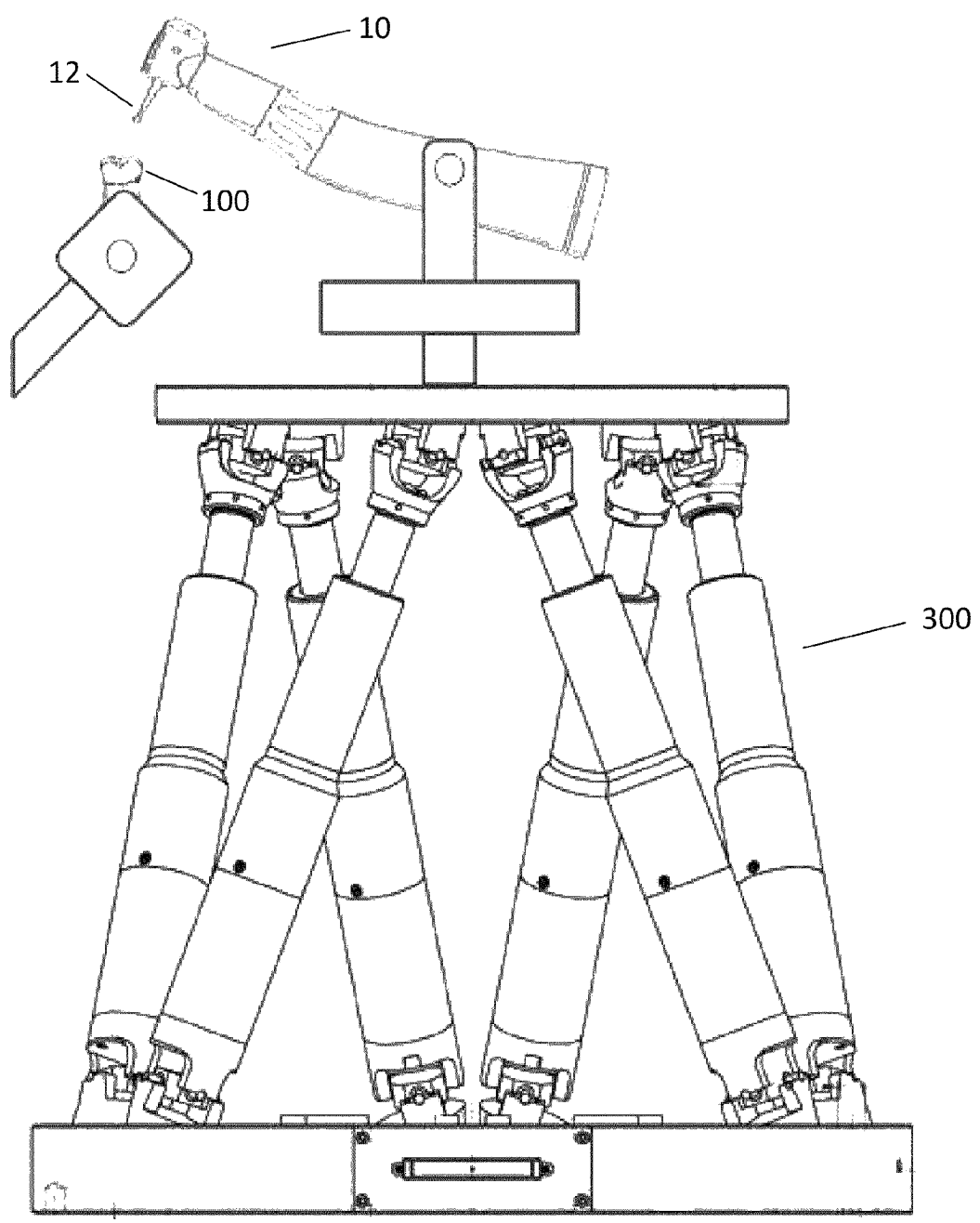
FIG. 11 illustrates an elevation view of a dental handpiece assembly according to an embodiment of the invention.

In one embodiment, the controller may desirably be tested first on known materials on a suitable controlled testing apparatus, such as the exemplary X-Y dental handpiece stage illustrated in FIG. 8. The minimum torque required to cut a particular dental material may be determined as a function of the applied cutting force. Then, additional samples with different material layers of dental materials may be fabricated in shapes of hollow and insert cylinders with tolerances that can be loosely fit, such as shown in FIG. 10, where a material (1) 110, material (2) 120 and intermediate layer 115 of dental material 100 is shown. Layers of flexible materials such as paper or Mylar may be wrapped around the insert to make a fit tight. This flexible material layer may desirably simulate the gray area that usually exists between tooth material, caries or decay, and restoration material layers in a tooth. Such multilayer samples may be tested on a suitable controlled test apparatus such as the X-Y dental handpiece stage shown in FIG. 8. In such an embodiment, the handpiece controller may be set to cut the hollow cylinder, pass the intermediate layer and stop at the insert cylinder. The cylinders may then be disassembled and weighed to monitor the accuracy and also tuning of the control parameters.

Figure 12:
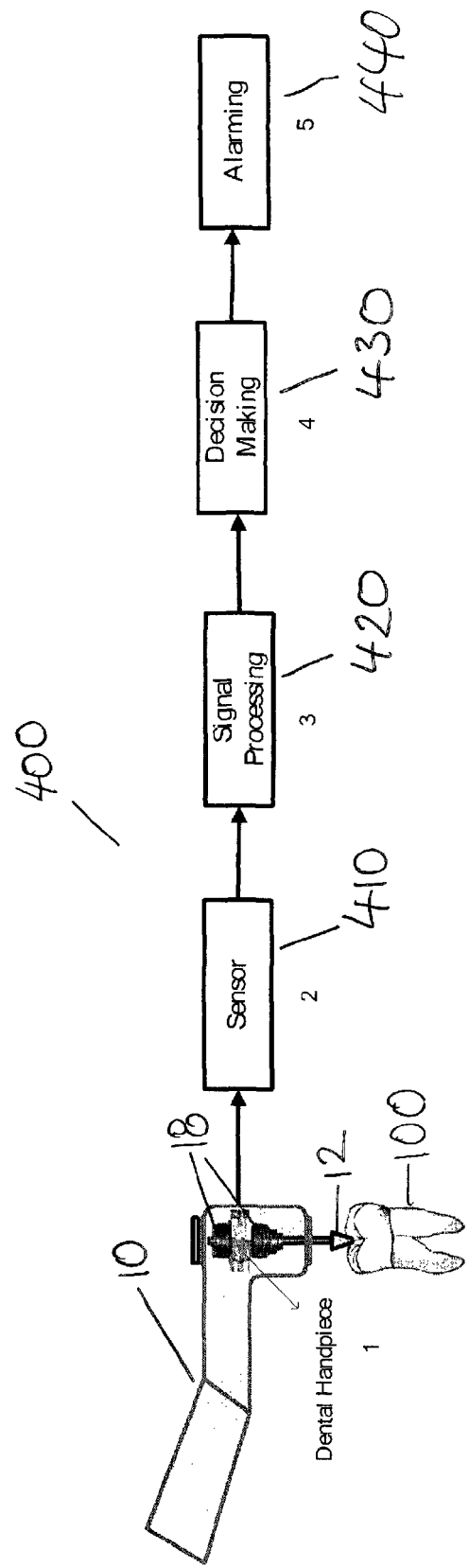
FIG. 12 illustrates a flow chart of the control method according to an embodiment of the invention.

In yet a further exemplary embodiment, to verify the control technique for controlling the cutting of a dental handpiece tool 10, a suitably responsive and flexible robotic actuator 300 may be used to produce fast and highly accurate trajectory tracking of a handpiece 10 in use to cut various materials in composite samples, for example. In one such embodiment, a P2000 hexapod™ parallel robot may be used for such purpose, as is shown in FIG. 12. In such an embodiment, the hexapod robot 300 may desirably produce fast and highly accurate trajectory tracking through six degrees of freedom. The hexapod robot 300 may desirably be integrated with a joystick (not shown) to command its motion during testing of the handpiece control system (not shown) comprising the handpiece, bur 12, power source (not shown) and controller (not shown). In such case, a common air turbine handpiece may be attached to the hexapod robot, such as with an adaptor plate, to hosts a suitably sensitive load cell, such as a Nono™ 17 6-axis load cell, for example. Samples of enamel, dentine, caries and dental restorations may then be placed inside an epoxy material for testing of the selective removal of dental materials using the dental handpiece control system of an embodiment of the invention, as described above. The epoxy sample may be weighed before and after the completion of the removal procedure to accurately determine material removal quantities.

Intelligent Dental Handpiece Control System Implementation

A intelligent dental handpiece according to one embodiment of the invention is adapted to discriminate between materials and to cut selectively. Providing real-time or online information about the material in the cutting process is an important component of such handpieces. It is known that the angular velocity of turbine handpieces decreases the moment its bur touches the material, however, the reduction in angular velocity is a function of both the material properties and the rate of advancement of the handpiece. A low advancement rate on a hard material can result the same reduction as a higher advancement rate on a softer material. As a result, knowing the angular velocity is not enough by itself to identify the material. The present inventive method according to one embodiment measures both quantities and compares the measured data to a pre-existing database and determine the tooth layer that dentists are removing in real-time. FIG. 12 depicts a flow chart of a control method comprising five steps, according to an embodiment of the invention.

Step 1: (Dental Handpiece): Any cutting device that is used in dentistry including electrical handpieces 10 (high/low speed, high/low torque), air-turbine handpieces 10, and the handpieces 10 that are used for dental implants may be employed in the handpiece control system 400. Existing devices may be retrofitted with sensor(s) 410, a signal processing unit 420 and decision making 430 and alarm communication 440. The alarm and control of drill speed steps are optional. The handpiece can work in either loaded (i.e. cutting a tooth/artificial tooth, etc.), or free running.

Step 2: (Sensing): While in operation, at least one sensor (contact or non-contact) 410 measures parameters relating to the handpiece 10 such as velocity, vibration, force, acceleration, torque, moment or other known parameter. The sensors 410 can include accelerometers, force sensors, microphones, Laser Doppler Vibrometers (LDV), thermal sensors, and other known sensors in the art. The preferred data for this invention according to a preferred embodiment are the handpiece vibrations and sounds during use. Therefore, a microphone which is an exemplary non-contact sensor 410 may be selected in one embodiment for sensing and data collection, because it does not require any changes to the current dental handpiece 10 design to acquire such data by non-contact means. The vibration sensor detects a vibration frequency signal produced by the handpiece 10 in operation.

Step 3 (Signal Processing): The control unit processes the signals obtained from the sensor unit, and performs an analysis on the data by applying a predetermined algorithm according to one embodiment. The control unit or signal processor 420 processes the vibration frequency signal and produces at least one secondary signal characteristic. The purpose of the signal processor/processing or control unit 420 is to extracting one or more features or secondary signal characteristics (typically two) from received signals, which may be indicative of different tooth structures. The applied force on the handpiece/cutting tool and the angular velocity and/or torque of the handpiece are two preferred choices for features or secondary signal characteristics for material discrimination purposes. The processing unit 420 may include or more of: computers, micro processors, micro controllers, data acquisition cards, and any programmable/programmed device that has data Input/Output ports, as is known in the art.

Step 4 (Decision Making): The processing unit or controller 430 compares the extracted features of the signal processing unit 420 to a database in order to discriminate between tooth structure, dental caries and dental restoration material. The controller 430 analyzes the secondary signal characteristic(s) and produces a control signal. After this comparison, the processing unit makes a determination about the quality of the cutting procedure. During the dental restorative refilling, or removing caries, the healthy parts of the tooth should not be cut. In addition, in installing the dental implants, it is also desirous to avoid unnecessary cuts which might damage the jaw nerves. The processing unit or controller 430 can identify such cuts.

Step 5 (Alarming/Controlling): The controller 430 acts appropriately based on the outcome of the decision making/controlling step. The final step optionally includes alarming signals 440 (either visual such as a light, or aural such as a tone or beep or alarm sound), or simply reducing the angular velocity of or stopping the dental handpiece. Operators can be notified of the alarm signal via one or more of voice, sound, an audible alarm, a visible alarm, a beep, light, or a visual display of at least one of said secondary signal characteristics, etc. A power controller (not shown) controls the angular velocity of the dental handpiece 10.

As described in the sections above, in an embodiment of the invention the intelligent dental handpiece control system may desirably incorporate online generation of material identification and control or modulation of cutting force and cutting power, to desirably provide a system to improve the selective control and removal of desired dental materials, while retaining dental materials and tooth structure that is not desired to be removed.

In an optional embodiment of the invention, a light indicator assistive dental handpiece control system may be provided, wherein the components and methods described above to identify dental materials being cut by frequency/time spectrum analysis of dental handpiece sounds, are used to provide a control signal identifying the dental material being cut to a dentist or other user, such as by illuminating lights with different colors, rather than by controlling the power of the handpiece directly. The color and intensity of lights illuminated in such an embodiment may desirably provide a dentist or other user with feedback about the type of dental material being cut by the handpiece at a given moment. In such an embodiment, the control system may further optionally be intermittently turned on and off accordingly for cases in which a user may or may not need assistance. Such an embodiment may also further be used as a training and introductory device in relation to an intelligent dental handpiece control system implementing control of the handpiece power, as described in embodiments above.

What is claimed is:

1. A dental handpiece apparatus comprising:
  a dental tool;
  a sensor operable to detect a frequency/time signal comprising one or more of a vibration, sound, force or torque frequency/time signal produced by said handpiece in use;

a signal processor operable to process said frequency/time signal and produce at least one secondary signal characteristic;

a controller operable to analyze said at least one secondary signal characteristic and identify a type of dental material in contact with said dental tool associated with said at least one secondary signal characteristic, and to produce a control signal corresponding to said type of dental material; and a power controller operable to control the angular velocity of the dental tool in response to the control signal.

2. The dental handpiece apparatus according to claim 1, wherein said sensor comprises at least one of: a microphone, a Laser Doppler Vibrometer and an accelerometer.

3. The dental handpiece apparatus according to claim 1, wherein said at least one secondary signal characteristic comprises at least one of: a force applied to said dental handpiece; and a cutting torque applied by said dental handpiece.

4. The dental handpiece apparatus according to claim 1, additionally comprising at least one control signal notification device operable to provide at least one warning signal to a user of said dental handpiece in response to said control signal.

5. The dental handpiece apparatus according to claim 1, wherein said power controller comprises at least one of: a pneumatic valve, a solenoid valve, and an electrical power supply.

6. The dental handpiece apparatus according to claim 4, wherein said at least one warning signal comprises at least one of: an audible alarm, a visible alarm, and a visual display corresponding to said type of dental material.

7. A method of controlling a dental handpiece comprising the steps of:

providing a dental tool rotatable by said handpiece;

sensing a frequency/time signal produced by said dental handpiece in use;

processing said frequency/time signal to determine at least one secondary signal characteristic;

analyzing said at least one secondary signal characteristic to identify a type of dental material in contact with said dental tool associated with said at least one secondary signal characteristic, and to determine a control signal corresponding to said type of dental material; and controlling the angular velocity of said dental tool in response to said control signal.

8. The method according to claim 7, wherein processing said frequency/time signal to determine at least one secondary signal characteristic additionally comprises determining at least one frequency peak of said frequency/time signal and determining said at least one secondary signal characteristic based on said at least one frequency peak.

9. The method according to claim 7, wherein said at least one secondary signal characteristic comprises at least one of: a force applied to said dental handpiece; and a cutting torque applied by said dental handpiece.

10. The method according to claim 7, wherein analyzing said at least one secondary signal characteristic to identify a type of dental material in contact with said dental tool associated with said at least one secondary signal characteristic, and to determine a control signal corresponding to said type of dental material additionally comprises comparing said at least one secondary signal characteristic with a database of known secondary signal characteristic values to identify a type of dental material.

11. The method according to claim 7, additionally comprising the step of: providing at least one warning signal to a user of said dental handpiece in response to said control signal.

12. The method according to claim 7, wherein controlling the angular velocity of said dental tool in response to said control signal additionally comprises at least one of: reducing the angular velocity of said dental tool and stopping said dental tool.

13. The method according to claim 11, wherein providing said at least one warning signal additionally comprises providing at least one of: an audible alarm, a visible alarm, and a visual display corresponding to said type of dental material to a user of said dental handpiece.

14. A dental handpiece control kit comprising:

a sensor operable to detect a frequency/time signal comprising at least one of a vibration, sound, torque or force frequency/time signal produced by said handpiece in use;

a signal processor operable to process said frequency/time signal and produce at least one secondary signal characteristic;

a controller operable to analyze said at least one secondary signal characteristic and identify a type of dental material in contact with said dental tool associated with said at least one secondary signal characteristic, and produce a control signal corresponding to said type of dental material; and a power controller operable to control the angular velocity of a dental tool rotated by the dental handpiece in response to said control signal.

15. The dental handpiece control kit according to claim 14, wherein said sensor comprises at least one of: a microphone; a Laser Doppler Vibrometer; and an accelerometer.

16. The dental handpiece control kit according to claim 14, wherein said at least one secondary signal characteristic comprises at least one of: a force applied to a dental handpiece; and a cutting torque applied by a dental handpiece.

17. The dental handpiece control kit according to claim 14, additionally comprising at least one control signal notification device operable to provide at least one warning signal to a user of a dental handpiece in response to said control signal.

18. The dental handpiece control kit according to claim 14, wherein said at least one warning signal comprises at least one of: an audible alarm, a visible alarm, and a visual display corresponding to said type of dental material.

19. The dental handpiece control kit according to claim 14, wherein said sensor is additionally adapted for attachment to an existing dental handpiece.

20. The dental handpiece control kit according to claim 14, wherein said sensor comprises a microphone, and said microphone is additionally adapted for installation at a location separate from a dental handpiece.

* * * * *